US009913679B2

(12) United States Patent
Gilbert et al.

(10) Patent No.: US 9,913,679 B2
(45) Date of Patent: Mar. 13, 2018

(54) ELECTROSURGICAL SYSTEMS AND METHODS FOR MONITORING POWER DOSAGE

(71) Applicant: COVIDIEN LP, Mansfield, MA (US)

(72) Inventors: James A. Gilbert, Boulder, CO (US); Patrick J. Digmann, Louisville, CO (US); Steven C. Rupp, Arvada, CO (US)

(73) Assignee: COVIDIEN LP, Mansfield, MA (US)

(*) Notice: Subject to any disclaimer, the term of this patent is extended or adjusted under 35 U.S.C. 154(b) by 740 days.

(21) Appl. No.: 14/447,049

(22) Filed: Jul. 30, 2014

(65) Prior Publication Data

US 2015/0105768 A1  Apr. 16, 2015

Related U.S. Application Data

(60) Provisional application No. 61/891,817, filed on Oct. 16, 2013.

(51) Int. Cl.
*A61B 18/12* (2006.01)
*A61B 18/00* (2006.01)

(52) U.S. Cl.
CPC ...... *A61B 18/1233* (2013.01); *A61B 18/1206* (2013.01); *A61B 2018/0063* (2013.01);
(Continued)

(58) Field of Classification Search
CPC . A61B 18/12; A61B 18/1206; A61B 18/1233; A61B 18/14; A61B 2018/00577;
(Continued)

(56) References Cited

U.S. PATENT DOCUMENTS 5,336,242 A * 8/1994 Zadeh ............... H03H 19/004
607/11
5,722,975 A * 3/1998 Edwards ............... A61B 18/12
606/34
(Continued)

FOREIGN PATENT DOCUMENTS

DE   179607 C   3/1905
DE   390937 C   3/1924
(Continued)

OTHER PUBLICATIONS

European Search Report issued in corresponding EP Application No. 14185328.3 dated Apr. 2, 2015.
(Continued)

*Primary Examiner* — Michael Peffley
*Assistant Examiner* — Khadijeh Vahdat

(57) ABSTRACT

The electrosurgical systems and methods of the present disclosure monitor power dosage delivered to tissue being treated with improved speed and accuracy. The electrosurgical systems include an output stage, sensors, analog all-pass filters, an analog multiplier, an average power calculation circuit, and a controller. The output stage generates electrosurgical energy to treat tissue. The plurality of sensors sense voltage and current waveforms of the generated electrosurgical energy. The plurality of analog all-pass filters filter the sensed voltage and current waveforms. The plurality of analog all-pass filter may have lagging or leading phase. The analog multiplier multiplies the filtered voltage and current waveforms to obtain a real power waveform. The average power calculation circuit calculates a real average power based on the real power waveform. The controller then generates a control signal to control the output stage based on the real average power.

17 Claims, 12 Drawing Sheets

(52) U.S. Cl.
CPC .............. *A61B 2018/00577* (2013.01); *A61B 2018/00589* (2013.01); *A61B 2018/00601* (2013.01); *A61B 2018/00648* (2013.01); *A61B 2018/00702* (2013.01); *A61B 2018/00779* (2013.01); *A61B 2018/00827* (2013.01); *A61B 2018/00869* (2013.01); *A61B 2018/00892* (2013.01)

(58) Field of Classification Search
CPC ........... A61B 2018/00589; A61B 2018/00601; A61B 2018/0063; A61B 2018/00648; A61B 2018/00702; A61B 2018/00779; A61B 2018/00827; A61B 2018/00869; A61B 2018/00892
USPC ...................................................... 606/33–41
See application file for complete search history.

(56) References Cited

U.S. PATENT DOCUMENTS

| | | |
|---|---|---|
| 7,300,435 B2 | 11/2007 | Wham et al. |
| D574,323 S | 8/2008 | Waaler |
| 7,554,341 B2 | 6/2009 | Eisele |
| 7,722,601 B2 | 5/2010 | Wham et al. |
| 7,777,567 B2 | 8/2010 | Polizzo |
| 7,846,156 B2 | 12/2010 | Malis et al. |
| 8,018,243 B2 | 9/2011 | Mann et al. |
| 8,576,013 B2 | 11/2013 | Coumou |
| 8,685,015 B2 | 4/2014 | Gilbert |
| 2005/0113819 A1 | 5/2005 | Wham et al. |
| 2006/0232471 A1 | 10/2006 | Coumou |
| 2007/0129716 A1 | 6/2007 | Daw et al. |
| 2011/0241773 A1 | 10/2011 | Fisk et al. |
| 2012/0265195 A1 | 10/2012 | Gilbert |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 390937 A1 | 10/1990 |
| EP | 0 556 705 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| EP | 2510895 A1 | 10/2012 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | H759794 A | 3/1995 |
| JP | H10504485 A | 5/1998 |
| JP | H11197158 A | 7/1999 |
| JP | 2002-065690 A | 3/2002 |
| JP | 2005-185657 A | 7/2005 |
| SU | 166452 | 11/1964 |
| SU | 727201 A2 | 4/1980 |
| WO | 9308756 A1 | 5/1993 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work; Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690 dated Apr. 3, 2003 inventor: Behnke.
U.S. Appl. No. 10/573,713 dated Mar. 28, 2006 inventor: Wham.
U.S. Appl. No. 10/761,524 dated Jan. 21, 2004 inventor: Wham.
U.S. Appl. No. 11/242,458 dated Oct. 3, 2005 inventor: Becker.
U.S. Appl. No. 14/096,341 dated Dec. 4, 2013 inventor: Johnson.
U.S. Appl. No. 14/098,859 dated Dec. 6, 2013 inventor: Johnson.
U.S. Appl. No. 14/100,113 dated Dec. 9, 2013 inventor: Gilbert.
U.S. Appl. No. 14/147,294 dated Jan. 3, 2014 inventor: Gilbert.
U.S. Appl. No. 14/147,312 dated Jan. 3, 2014 inventor: Gilbert.
U.S. Appl. No. 14/168,296 dated Jan. 30, 2014, inventor: Mattmiller.
U.S. Appl. No. 14/174,551 dated Feb. 6, 2014 inventor: Johnson.
U.S. Appl. No. 14/174,607 dated Feb. 6, 2014 inventor: Friedrichs.
U.S. Appl. No. 14/179,724 dated Feb. 13, 2014 inventor: Johnson.
U.S. Appl. No. 14/180,965 dated Feb. 14, 2014 inventor: Larson.
U.S. Appl. No. 14/181,114 dated Feb. 14, 2014 inventor: Larson.
U.S. Appl. No. 14/182,797 dated Feb. 18, 2014 inventor: Wham.
U.S. Appl. No. 14/190,830 dated Feb. 26, 2014 inventor: Johnson.
U.S. Appl. No. 14/190,895 dated Feb. 26, 2014 inventor: Gilbert.
U.S. Appl. No. 14/255,051 dated Apr. 17, 2014 inventor: Coulson.
U.S. Appl. No. 14/262,219 dated Apr. 25, 2014, inventor: Gilbert.
U.S. Appl. No. 14/267,066 dated May 1, 2014, inventor: Friedrichs.
U.S. Appl. No. 14/268,187 dated May 2, 2014, inventor: Kerr.
U.S. Appl. No. 14/283,604 dated May 21, 2014, inventor: Behnke.
U.S. Appl. No. 14/297,771 dated Jun. 6, 2014, inventor: Wham.
U.S. Appl. No. 14/297,812 dated Jun. 6, 2014, inventor: Wham.
U.S. Appl. No. 14/297,890 dated Jun. 6, 2014, inventor: Wham.
U.S. Appl. No. 14/320,762 dated Jul. 1, 2014, inventor: Gilbert.
U.S. Appl. No. 14/320,804 dated Jul. 1, 2014, inventor: Gilbert.
European Office Action dated Sep. 26, 2017 in corresponding European Patent Application No. 14185328.3, 9 pages.

* cited by examiner

ELECTROSURGICAL SYSTEMS AND METHODS FOR MONITORING POWER DOSAGE

CROSS REFERENCE TO RELATED APPLICATION

The present application claims the benefit of and priority to U.S. Provisional Application Ser. No. 61/891,817, filed on Oct. 16, 2013, the entire contents of which are incorporated herein by reference.

BACKGROUND

1. Technical Field

The present disclosure generally relates to electrosurgery. More particularly, the present disclosure relates to electrosurgical systems and methods for monitoring power dosage of electrosurgical energy delivered to tissue.

2. Background of Related Art

Electrosurgery involves the application of high-frequency electric current to cut or modify biological tissue during an electrosurgical operation. Electrosurgery is performed using an electrosurgical generator, an active electrode, and a return electrode. The electrosurgical generator (also referred to as a power supply or waveform generator) generates an alternating current (AC), which is applied to a patient's tissue through the active electrode and is returned to the electrosurgical generator through the return electrode. The AC typically has a frequency above 100 kilohertz (kHz) to avoid muscle and/or nerve stimulation.

During electrosurgery, the AC generated by the electrosurgical generator is conducted through tissue disposed between the active and return electrodes. The electrical energy (also referred to as electrosurgical energy) delivered to the tissue is converted into heat due to the resistivity of the tissue, which causes the tissue temperature to rise. The electrosurgical generator monitors the dosage of power (i.e., electrical energy per time) to control the heating of the tissue. Although many other variables affect the total heating of the tissue, increased current density and resistance of the tissue usually lead to increased heating. The electrosurgical energy is typically used for cutting, dissecting, ablating, coagulating, and/or sealing tissue.

The two basic types of electrosurgery employed are monopolar and bipolar electrosurgery. Both of these types of electrosurgery use an active electrode and a return electrode. In bipolar electrosurgery, the surgical instrument includes an active electrode and a return electrode on the same instrument or in very close proximity to one another, which cause current to flow through a small amount of tissue. In monopolar electrosurgery, the return electrode is located elsewhere on the patient's body and is typically not a part of the electrosurgical instrument itself. In monopolar electrosurgery, the return electrode is part of a device typically referred to as a return pad.

An electrosurgical generator makes use of voltage and current sensors to measure quantities, such as power, for controlling the output of the electrosurgical generator to achieve a desired clinical effect. A cable, which may be more than a meter in length, connects the electrosurgical generator to the active and return electrodes and is used to deliver electrosurgical energy to tissue being treated. The cable creates a circuit network between the voltage and current sensors and the tissue being treated, which distorts the voltage and current waveforms generated by the electrosurgical generator so that the waveforms deviate from the desired pure sinusoidal, rectangular, sawtooth, pulse, triangular, or blended waveforms commonly used for electrosurgery. Thus, to more accurately monitor power, many generators employ compensation algorithms that account for the impedance of the circuit network of the cable.

These compensation algorithms typically involve complex computations, which may be computationally inefficient and expensive. As a result, the real-time embedded software systems that perform the complex computations introduce time delays into the control algorithms for controlling the electrosurgical generator. When these time delays are accumulated, the generator may under-deliver or over-deliver electrosurgical energy to the tissue being treated.

SUMMARY

The electrosurgical systems and methods of the present disclosure monitor power dosage delivered to tissue being treated with improved speed and accuracy. The electrosurgical systems and methods use analog filters for sensor and/or cable compensation.

In one aspect, the electrosurgical systems include an output stage, sensors, analog all-pass filters, an analog multiplier, an average power calculation circuit, and a controller. The output stage generates electrosurgical energy to treat the tissue. The sensors sense voltage and current waveforms of the generated electrosurgical energy. The analog all-pass filters filter the sensed voltage and current waveforms. The plurality of analog all-pass filter may have a lagging or leading phase. The analog multiplier multiplies the filtered voltage and current waveforms to obtain a real power waveform. The average power calculation circuit calculates a real average power based on the real power waveform. The controller then generates a control signal to control the output stage based on the real average power.

The average power calculation circuit may include an analog integrator, an analog-to-digital (ADC), and a digital averaging filter. The analog integrator integrates the real power waveform. The ADC converts the integrated real power waveform into digital power waveform data. The digital averaging filter calculates the real average power based on the digital power waveform data. The digital averaging filter may be a moving average filter and be a finite or infinite impulse response filter.

The average power calculation circuit may include an analog low pass filter, an ADC, and a digital integrator. The analog low pass filter filters the real power waveform and the ADC digitally samples the filtered power waveform into digital power waveform data. The digital integrator integrates the digital power waveform data to calculate the real average power.

The analog all-pass filters includes a resistor and a capacitor to compensate for the phase difference between the voltage and current waveforms. The resistor may be a variable resistor to continuously adjust the phase difference between the voltage and current waveforms.

The plurality of analog all-pass filters may be first-order all-pass filters or second order all-pass filters. The second-order all-pass filter may include at least one bandpass filter which can be a multiple feedback bandpass filter, dual amplifier bandpass filter, or biquad filter.

The present disclosure, in another aspect, features a method for controlling an electrosurgical generator. The method includes generating electrosurgical energy, sensing a voltage waveform and a current waveform of the generated electrosurgical energy, filtering the sensed voltage and current waveforms by analog all-pass filters, multiplying the filtered voltage and current waveforms to obtain a real power waveform, calculating a real average power based on the real power waveform, and generating a control signal to control the output stage based on the real average power.

The present disclosure, in another aspect, features a non-transitory computer-readable medium storing instructions that, when executed by a processor, implement a method for controlling an electrosurgical generator. The method includes generating electrosurgical energy, sensing a voltage waveform and a current waveform of the generated electrosurgical energy, filtering the sensed voltage and current waveforms by analog all-pass filters, multiplying the filtered voltage and current waveforms to obtain a real power waveform, calculating a real average power based on the real power waveform, and generating a control signal to control the output stage based on the real average power.

BRIEF DESCRIPTION OF THE DRAWINGS

Various embodiment of the present disclosure are described with reference to the accompanying drawings wherein.

DETAILED DESCRIPTION

As described above, the electrosurgical generator circuitry and the cable in an electrosurgical system create a circuit network between the voltage and current sensors and the tissue being treated, which causes inaccurate power and impedance measurements. Thus, to more accurately measure power dissipated in and impedance of the tissue being treated, many generators employ compensation algorithms that account for the impedance of the circuit network. These compensation algorithms involve the measurement and storage of multiple cable parameters, such as series inductance, shunt capacitance, and resistance, which are used as constants in the solutions to the circuit network. The compensation algorithms also involve many mathematical operations, e.g., multiplies and additions, on complex numbers having real and imaginary components.

The electrosurgical systems and methods of the present disclosure reduce the amount of memory and processing power needed to accurately measure real average power actually delivered to the tissue. The systems and methods according to the present disclosure use analog all-pass filters having leading or lagging phase to compensate for distortions caused by the circuit network so that the measured voltage and current can more accurately represent the actual voltage and current delivered to the tissue.

Figure 1:
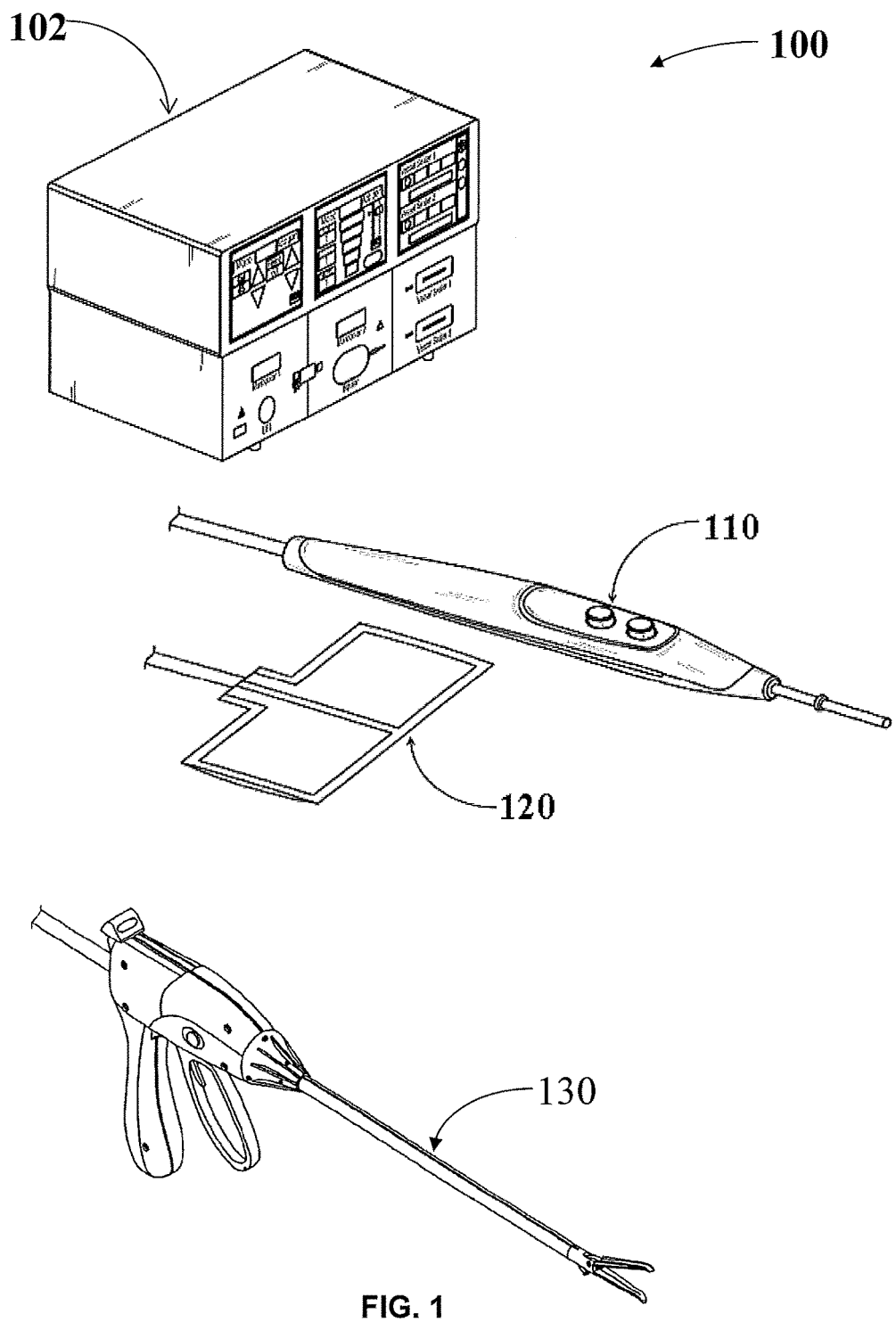
FIG. 1 is an electrosurgical system including an electrosurgical generator in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy to treat tissue of a patient. The electrosurgical generator 102 generates an appropriate level of electrosurgical energy based on the selected mode of operation (e.g., cutting, coagulating, ablating, or sealing) and/or the sensed voltage and current waveforms of the generated electrosurgical energy. The electrosurgical system 100 may also include output connectors corresponding to a variety of electrosurgical instruments.

The electrosurgical system 100 further includes a monopolar electrosurgical instrument 110 having an electrode for treating tissue of the patient (e.g., an electrosurgical cutting probe or ablation electrode) with a return pad 120. The monopolar electrosurgical instrument 110 can be connected to the electrosurgical generator 102 via one of the output connectors. The electrosurgical generator 102 may generate electrosurgical energy in the form of radio frequency (RF) energy. The electrosurgical energy is supplied to the monopolar electrosurgical instrument 110, which applies the electrosurgical energy to tissue. The electrosurgical energy is returned to the electrosurgical generator 102 through the return pad 120. The return pad 120 provides sufficient contact area with the patient's tissue so as to minimize the risk of tissue damage due to the electrosurgical energy applied to the tissue.

The electrosurgical system 100 also includes a bipolar electrosurgical instrument 130. The bipolar electrosurgical instrument 130 can be connected to the electrosurgical generator 102 via one of the output connectors. The electrosurgical energy is supplied to one of the two forceps, is applied to tissue, and is returned to the electrosurgical generator 102 through the other forceps.

The electrosurgical generator 102 may be any suitable type of generator and may include output connectors to accommodate various types of electrosurgical instruments (e.g., monopolar electrosurgical instrument 110 and bipolar electrosurgical instrument 130). The electrosurgical generator 102 may also be configured to operate in a variety of modes, such as ablation, cutting, coagulation, and sealing. The electrosurgical generator 102 may include a switching mechanism (e.g., relays) to switch the supply of RF energy among the output connectors to which various electrosurgical instruments may be connected. For example, when an electrosurgical instrument 110 is connected to the electrosurgical generator 102, the switching mechanism switches the supply of RF energy to the monopolar plug. In embodiments, the electrosurgical generator 102 may be configured to provide RF energy to a plurality instruments simultaneously.

The electrosurgical generator 102 includes a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular surgical procedure (e.g., coagulating, ablating, tissue sealing, or cutting). The electrosurgical instruments 110 and 130 may also include user controls. In addition, the electrosurgical generator 102 may include one or more display screens for displaying a variety of information related to the operation of the electrosurgical generator 102 (e.g., intensity settings and treatment complete indicators).

Figure 2:
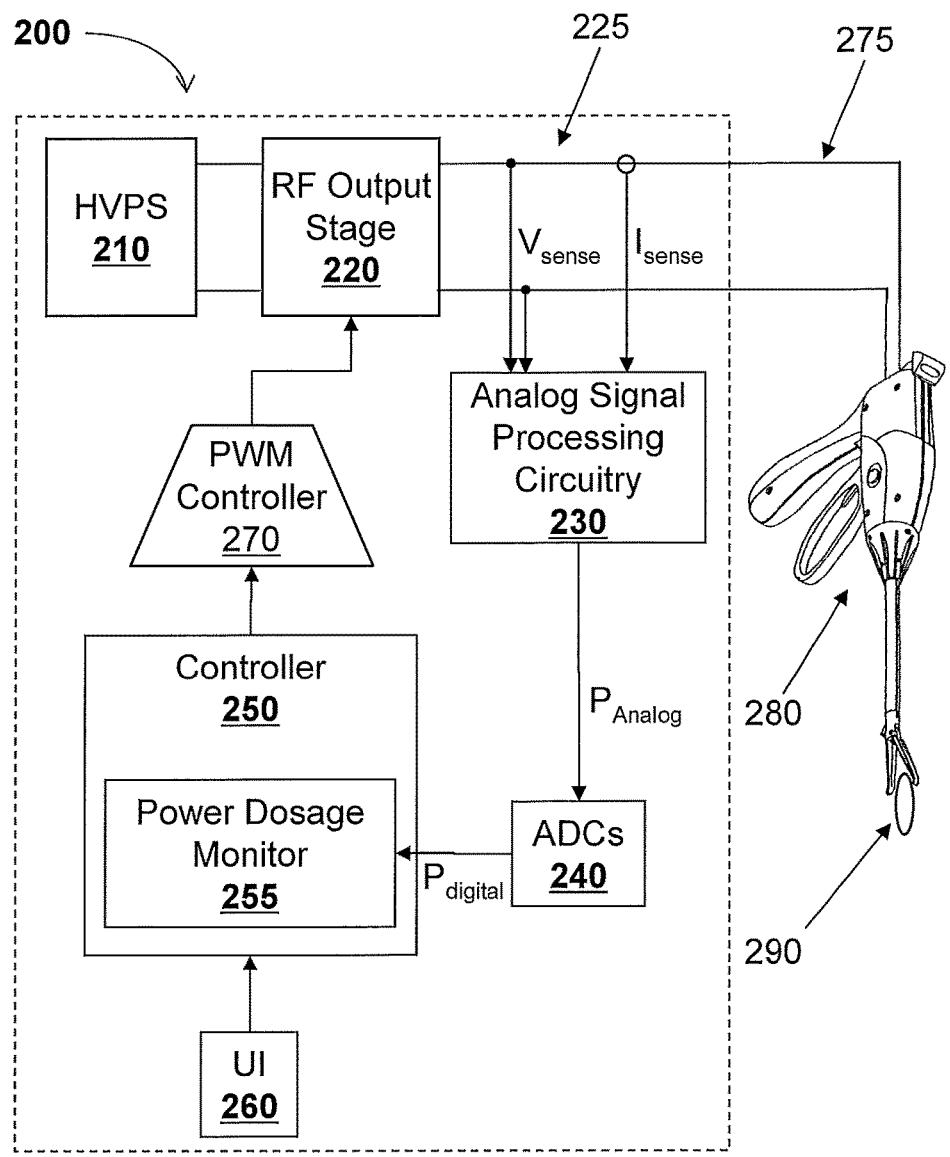
FIG. 2 is a block diagram of the generator circuitry of the electrosurgical generator connected to the instrument 130 of the electrosurgical system of FIG. 1.

FIG. 2 is a block circuit diagram of the electrosurgical generator 102 of FIG. 1. The electrosurgical generator 102 includes a generator circuit 200, which is connected to a cable 275 of an electrosurgical instrument 280 that delivers electrosurgical energy to treat tissue 290. The generator circuit 200 includes a high voltage power supply (HVPS) 210, a radio frequency (RF) output stage 220, voltage and current sensors 225, an analog signal processing circuit 230, analog-to-digital converters (ADCs) 240, a controller 250, a user interface (UI) 260, and a pulse width modulation controller 270. The generator circuit 200 is configured to connect to an AC power source, such as a power outlet, which generates AC having a low frequency (e.g., 50 Hz or 60 Hz). The AC power source provides AC power to the generator circuit 200, which converts the low frequency AC to higher frequency AC that is suitable for a desired electrosurgical procedure. Specifically, the HVPS 210 and the RF output stage 220 convert the AC having a low frequency to direct current and then invert the DC to AC having a high frequency. The generated AC waveform has a frequency suitable for an electrosurgical procedure (e.g., 472 kHz, 200 kHz, and 390 kHz).

The appropriate frequency for the electrosurgical energy may differ based on the electrosurgical procedures and modes of electrosurgery. For example, nerve and muscle stimulations cease at about 100,000 cycles per second (100 kHz) and some electrosurgical procedures can be performed safely at a radio frequency (RF) above 100 kHz. At frequencies over 100 kHz, the electrosurgical energy can pass through a patient to targeted tissue with minimal neuromuscular stimulation. For example, ablation uses a frequency of 472 kHz. Other electrosurgical procedures can be performed at frequencies lower than 472 kHz, e.g., 200 kHz or 390 kHz, with minimal risk of damaging nerves and muscles. The HVPS 210 and the RF output stage 220 can provide AC signals with various frequencies suitable for electrosurgical operations. The RF output stage 220 may include a resonant tank circuit that matches the impedance at the RF output stage 220 to the impedance of the cable 275 and the tissue 290 so that there is a maximum or optimum power transfer from the electrosurgical generator 102 to the tissue 290.

The plurality of voltage and current sensors 225 sense the AC voltage and current waveforms generated by the HVPS 210 and the RF output stage 220. The plurality of sensors 225 are coupled to the RF output stage 220 and the cable 275 to sense the voltage and current output from the generator circuit 200 to the cable 275. In particular, voltage sensors measure voltage across the two output connecting wires of the RF output stage 220 to the cable 275 and current sensors measure current passing through at least one output connecting wire of the RF output stage 220 to the cable 275.

The plurality of sensors 225 may include two or more pairs or sets of voltage and current sensors that provide redundant measurements of the voltage and current waveforms. This redundancy ensures the reliability, accuracy, and stability of the voltage and current measurements at the output of the RF output stage 220. In embodiments, the sensors 225 may include fewer or more sets of voltage and current sensors depending on the application or the design requirements.

The current and voltage sensed by the sensors 225 are not the same as the current and voltage delivered to the tissue 290 because the cable 275 introduces an impedance between the sensors 225 and the tissue 290 and/or because the voltage and current sensors themselves have inaccuracies. The sensed voltage and current waveforms are provided to the analog signal processing circuit 230 which differentially phase-compensates for the impedance of the cable and/or the sensor inaccuracies. The analog signal processing circuit 230 outputs an analog power waveform, as described in more detail below.

The analog power waveform is then sampled by the ADCs 240 to obtain digital samples of the power waveform. The plurality of ADCs 240 may sample the analog power waveform at a frequency that is an integer multiple of the frequency of the voltage and current waveforms generated by the RF output stage 220. The digital samples of the power waveform are provided to the controller 250.

The controller 250 includes a power dosage monitor 255 that receives the digital samples of the power waveform from the ADCs 240 and determines the real average power delivered to the tissue 290 being treated. The controller 250 compares the measured real average power with a power profile specific for an electrosurgical operation and generates a control signal to the PWM controller 270. The PWM controller 270 then generates a PWM signal having a desired duty cycle to control the output of the RF output stage 220.

The controller 250 also receives input from the user interface (UI) 260. A user may set an electrosurgical operation mode (e.g., cutting, coagulating, ablating, or sealing) and corresponding electrosurgical signal type (e.g., pure sinusoidal, rectangular, sawtooth, pulse, triangular, or blended waveforms) via the UI 260. The UI 260 is not limited to setting the above features but allows a user to select a type of electrosurgical procedure (e.g., monopolar or bipolar), or to input desired control parameters for the electrosurgical procedure or the mode. The controller 250 may incorporate the inputs from the UI 260 to select an appropriate power profile and to generate a control signal.

Figure 3:
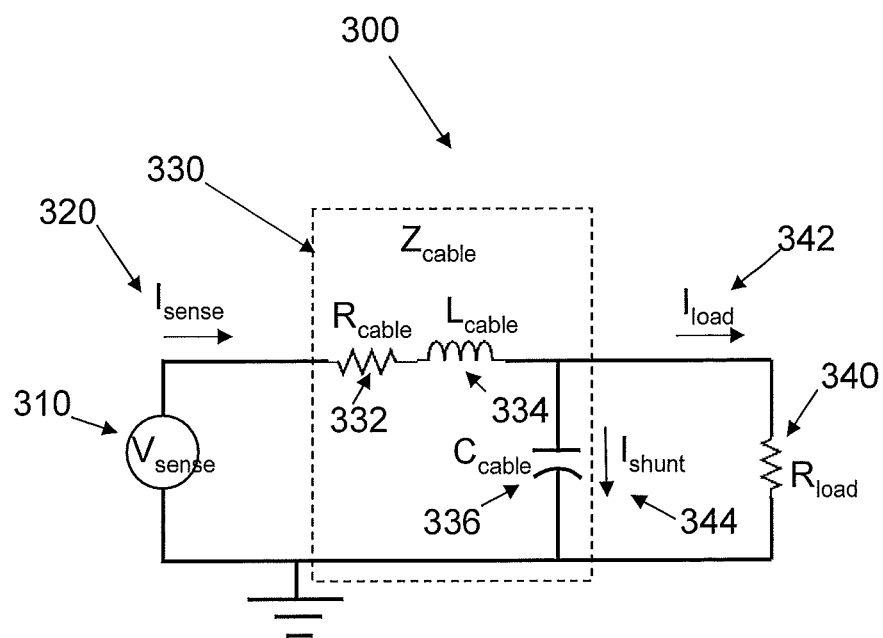
FIG. 3 is a circuit diagram illustrating an impedance model of the cable 275 of FIG. 2.

FIG. 3 is a circuit diagram of an impedance model of the cable 275 of FIG. 2. The plurality of sensors sense voltage $V_{sense}$ 310 and current $I_{sense}$ 320. The cable 275 has an impedance $Z_{cable}$ 330 that includes a resistance $R_{cable}$ 332, an inductance $L_{cable}$ 334, and a shunt capacitance $C_{cable}$ 336. The tissue 290 is resistive in typical electrosurgical procedures and thus is modeled as a load resistance $R_{load}$ 340.

One of the sensors 225 sense current $I_{sense}$ 320 passing through the supply line or return line of the electrosurgical generator 102 and another one of the sensors 225 senses voltage $V_{sense}$ 310 across the supply and return lines of the electrosurgical generator 102. The sensed voltage $V_{sense}$ 310 drops across the cable resistance $R_{cable}$ 332. The current $I_{sense}$ 320 is divided into shunt current $I_{shunt}$ 344 passing through the shunt capacitance $C_{cable}$ 236 and load current $I_{load}$ 342 passing through the load resistance $R_{load}$ 340. Thus, the sensed current $I_{sense}$ 320 is different from the current passing through the tissue load resistance $R_{load}$ 340. Similarly, the sensed voltage $V_{sense}$ 310 is different from the voltage across the tissue load resistance $R_{load}$ 340 due to the cable resistance $R_{cable}$ 332 and the cable inductance $L_{cable}$ 334. It follows that power calculated from the sensed voltage and current waveforms is also different from the actual power delivered to the tissue.

Additionally, the impedance of the cable, $Z_{cable}$ 330, also distorts the phase of the sensed voltage and current waveforms so that the power calculated from the sensed voltage and current waveforms has a complex value having a real part and an imaginary part. Assuming that the cable resistance $R_{cable}$ 332 is negligibly small compared to the load resistance $R_{load}$ 340 and that the shunt current $I_{shunt}$ 344 encounters no other resistance or loss, the real part of the complex power may be considered the power delivered to the tissue $R_{load}$ 340. Moreover, the sensors may distort the phase and magnitude of the voltage and current. The systems and methods of the present disclosure employ cable and sensor compensation techniques to accurately measure the real part of the power sensed by the sensors 225, which may represent the power delivered to the tissue. These cable and sensor compensation techniques compensate for the phase difference between the sensed voltage and current waveforms by using all-pass filters.

Figure 4A:
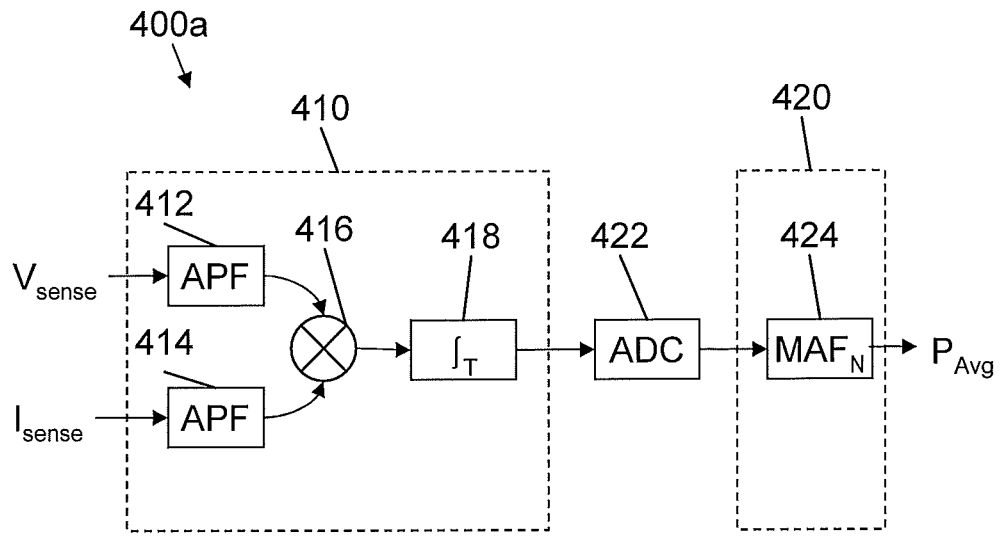
FIGS. 4A-4C are block diagrams of analog and digital signal processing circuits of the electrosurgical generator of FIG. 2 including all-pass filters in accordance with embodiments of the present disclosure.
Figure 4B:
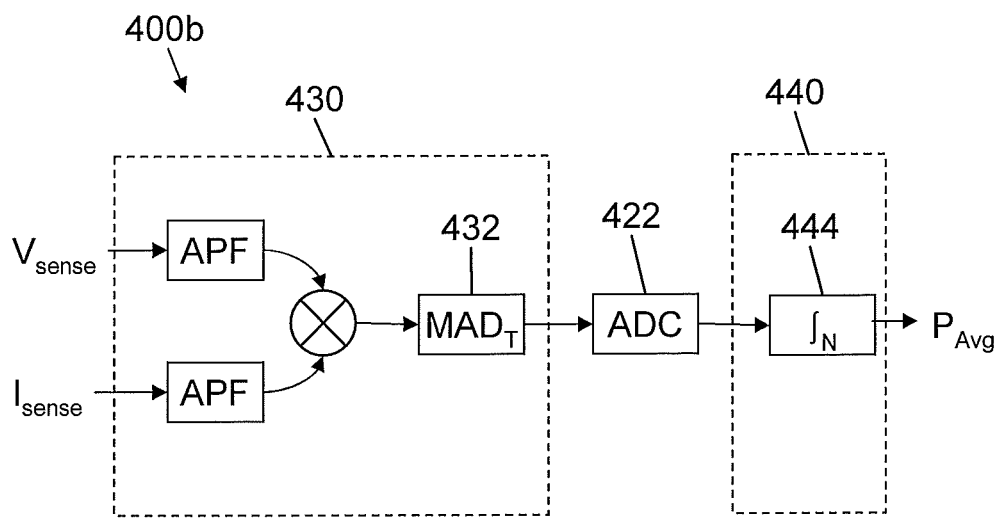
Figure 4C:
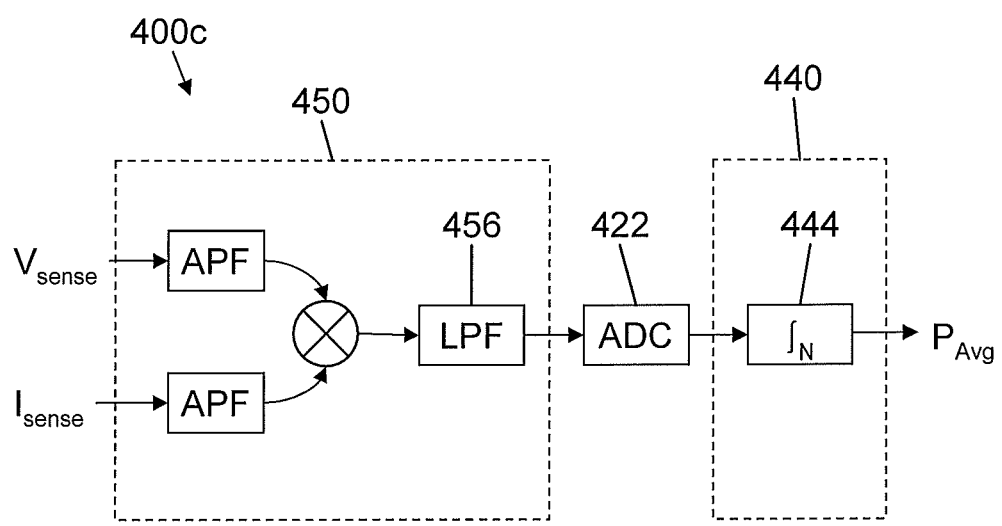

FIGS. 4A-4C are circuit block diagrams of power monitoring circuits for monitoring power dosage according to embodiments of the present disclosure. These circuit block diagrams include analog circuits, analog-to-digital converters (ADCs), and digital circuits for monitoring power dosage. The analog circuits include all-pass filters, a multiplier, and an analog averaging filter. As described below, the analog averaging filter may be substituted for a low-pass filter or an analog integrator. The digital circuits may include a digital averaging filter or a digital integrator.

FIG. 4A is a circuit block diagram of a power calculation circuit 400a for calculating average power delivered to the tissue being treated according to an embodiment of the present disclosure. The power calculation circuit 400a includes an analog circuit 410 for processing the voltage and current sensor signals, an analog-to-digital converter (ADC) 422 for converting the analog signal output from the analog circuit 410 into a digital signal, and a digital circuit 420 for processing the digital signal. The analog circuit 410 includes all-pass filters (APFs) 412, 414, a multiplier 416, and an integrator 418. A voltage waveform sensed by a voltage sensor is provided to the APF 412 and a current waveform sensed by a current sensor is provided to the APF 414. The outputs from the APFs 412 and 414 are multiplied by the multiplier 416 to obtain an analog power waveform. The APFs 412 and 414 are described in more detail below with reference to FIGS. 5A-9.

The integrator 418 integrates the analog power waveform for a certain period T, which is an integer multiple of the period of the carrier frequency. For example, if a carrier frequency is 472 kHz, then the period T is an integer multiple of the reciprocal of the carrier frequency, i.e., about 2.12 µs. The integrator 418 also cancels out noise components which are considered to have a higher frequency than the carrier frequency. Since noise components vary about the desired power waveform during the period T, the signal noise is cancelled out when added together.

The analog power waveform output from the analog circuit 410 is provided to the ADC 422, which converts the analog power waveform into a digital power waveform. The digital power waveform is then fed to a moving average filter 424 of digital circuit 420. The ADC 422 samples K digital samples of the analog average power waveform for the carrier period, where K is an integer number. For example, the ADC 422 samples at least one or more digital samples for about 2.12 µs in the case where the carrier frequency is 472 kHz. The moving average filter 424 receives and averages the digital power waveform to obtain the average power delivered to and consumed by the tissue.

The moving average filter 424 may be an infinite impulse response filter or a finite impulse response filter. The moving average filter 424 averages N samples for the carrier period, where N is an integer number. The output of the digital moving average filter 424 is the real average power to the tissue during the carrier period. The controller 250 of the electrosurgical generator 200 monitors the real average power and generates a control signal to control the output of the electrosurgical generator 200.

FIG. 4B is a circuit block diagram of a power calculation circuit 400b according to another embodiment of the present disclosure. The power calculation circuit 400b includes an analog circuit 430, an ADC 422, and a digital circuit 440. The analog circuit 430 includes the APFs 412, 414, the multiplier 416, and an analog mean absolute deviation (MAD) circuit 432. The digital circuitry 440 includes a digital integrator 444. The analog power waveform generated by the multiplier 416 is provided to the analog mean absolute deviation circuit 432 that rectifies and averages the analog power waveform for the carrier period T. Because the carrier period T is generally longer than the period of the noise component, the analog mean absolute deviation (MAD) circuit 432 cancels out the noise component. In other embodiments, the MAD circuit 432 may be replaced by any other precision rectifier or analog RMS-DC circuit known to those having skill in the art.

The analog power waveform output from the analog circuit 430 is sampled by the ADC 422 to obtain a digital power waveform. The digital integrator 444 integrates the digital power waveform over N samples of the period of the carrier signal. The result of the digital integrator 444 is the real average power delivered to and consumed by the tissue being treated.

FIG. 4C shows a circuit block diagram of a power calculation circuit 400c according to another embodiment of the present disclosure. The difference between power calculation circuit 400c and the power calculation circuit 400b of FIG. 4B is that the power calculation circuit 400c includes an analog low-pass filter (LPF) 456 instead of the analog mean absolute deviation circuit 432. The LPF 456 passes baseband frequencies of the analog power waveform and filters out high frequency noise. Thus, as shown in FIGS. 4A-4C, a variety of electronic components, e.g., an analog integrator 418, an analog mean absolute deviation circuit 432, or a low pass filter 456, may be employed to filter out noise.

Figure 5A:
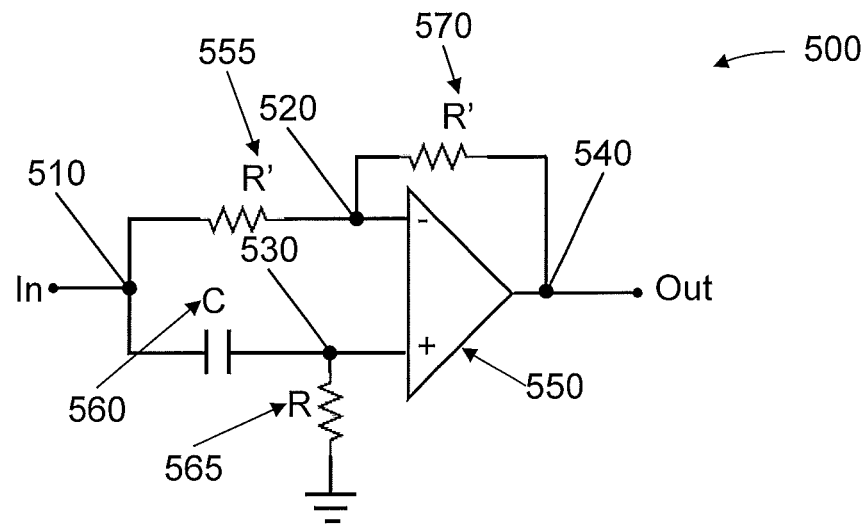
FIGS. 5A-5B are circuit diagrams of all-pass filters that may be employed in the power calculation circuits of FIGS. 4A-4C.
Figure 5B:
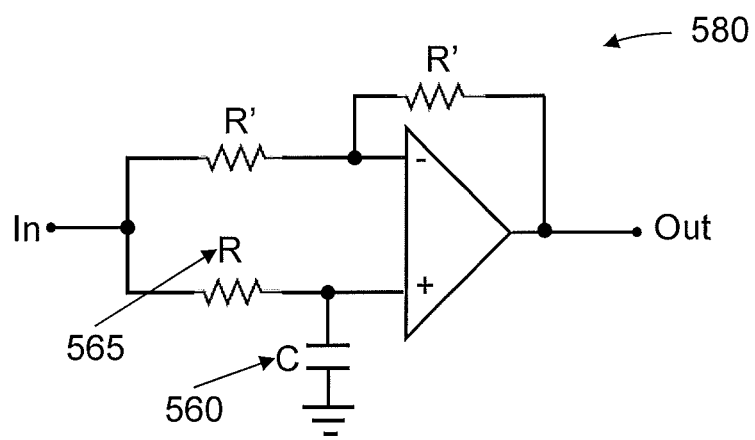

FIGS. 5A and 5B are circuit diagrams of APFs that may be employed in the power monitoring circuits of FIGS. 4A-4C. FIG. 5A illustrates a lagging phase APF 500 that includes an operational amplifier (op-amp) 550, an RC circuit having a capacitor 560 and a resistor 565 coupled to the non-inverting input of the op-amp 550, and resistors 555 and 570 coupled to the inverting input for setting the gain to 1. Op-amps generally amplify the difference between voltage $V_+$ at the non-inverting input and voltage $V_-$ at the inverting input in accordance with the gain of the op-amp as follows:

$$V_{Out} = A \cdot (V_+ - V_-),$$

where $V_{out}$ is the output voltage of the op-amp 550 and A is the gain of the op-amp 550.

The APF 500 includes input node 510, inverting input node 520, non-inverting input node 530, and output node 540. The resistor 555 is connected between the input node 510 and the inverting input node 520, and another resistor 570, as a feedback resistor, is connected between the inverting input node 520 and the output node 540. Capacitor 560 is connected between the input node 510 and the non-inverting input node 530, and resistor 565 is connected between the non-inverting input node 530 and the ground. Due to characteristics of the capacitor 560, the phase of input voltage at the non-inverting input of the op-amp 550 is a lagging phase and the phase of the output voltage at the output node 540 is also a lagging phase.

The voltage $V_{in}$ at the non-inverting input node 530 is calculated by the voltage divider principle in the time domain as follows:

$$V_+ = V_{in} \frac{R}{R + \frac{1}{j\omega C}},$$

where R is the resistance value of the resistor 565, ω is the angular frequency of the input voltage $V_{in}$, and C is the capacitance value of the capacitor 560. In a similar manner, the input voltage $V_{in}$ is calculated in frequency domain as follows:

$$V_+ = V_{in} \frac{R}{R + \frac{1}{sC}}$$

where s is a variable in the complex Laplace domain.

Since the resistance values R' of the two resistors 555 and 570 are same, the gain of the inverting input of the op-amp is negative one. This gain may be adjusted up or down to compensate for any sensor or cable gain inaccuracies. Thus, the transfer function H(s) of the APF 500 is calculated as follows:

$$H(s) = \frac{2R}{R + \frac{1}{sC}} - 1 = \frac{2sRC}{sRC + 1} - 1 = \frac{sRC - 1}{sRC + 1}.$$

The gain G of the transfer function H(s) is calculated by obtaining a magnitude of the transfer function H(jω) as follows:

$$G = |H(j\omega)| = \left|\frac{j\omega RC - 1}{j\omega RC + 1}\right| = \left|\frac{(\omega^2 R^2 C^2 - 1) + 2j\omega RC}{\omega^2 R^2 C^2 + 1}\right|.$$

The magnitude of a complex number is a square root value of the sum of squares of the real and imaginary parts of the complex number. Thus, the gain G of the transfer function H(jω) is one:

$$G = \frac{1}{\omega^2 R^2 C^2 + 1} \sqrt{(\omega^2 R^2 C^2 + 1)^2 + (2\omega RC)^2} =$$
$$\frac{1}{\omega^2 R^2 C^2 + 1} \sqrt{(\omega^2 R^2 C^2 + 1)^2} = 1.$$

The phase of the transfer function H(jω) is given by the following equation:

$$\angle H(j\omega) = 180 - 2 \arctan(\omega RC).$$

While the APF 550 passes all signals, the current waveform lags behind the voltage waveform. The phase lag $\Delta\phi(\omega)$ of the transfer function H(jω) is calculated according to the following equation:

$$\Delta\phi(\omega) = -2 \arctan(\omega RC).$$

Since the phase lag $\Delta\phi(\omega)$ is dependent on the resistance value R and the capacitance value C, the APF 500 can control the phase lag $\Delta\phi(\omega)$ by changing the resistance value R of the resistor 565 and the capacitance value C of the capacitor 560 based on the angular frequency of the input voltage or current waveform. For example, when the angular frequency ω is relatively high compared to the resistance R and the capacitance C, then the phase lag $\Delta\phi(\omega)$ would be almost 180 degrees. Thus, there would be no phase shift in the actual voltage and current waveforms. On the other hand, when the angular frequency ω is relatively low compared to the resistance R and the capacitance C, then the phase lag $\Delta\phi(\omega)$ would be almost 0 degrees. Thus, there would be almost 180 degrees of phase shift in the voltage and current waveforms. Thus, by changing the resistance value R and capacitance value C corresponding to the angular frequency ω, the phase lag $\Delta\phi(\omega)$ can be controlled.

When a circuit network, which includes sensors and a cable attached to the electrosurgical generator, causes a phase shift in the generated electrosurgical energy and the phase shift is within a manageable range, the phase shift may be compensated by adding APFs that include a resistor having an appropriate resistance value and a capacitor having an appropriate capacitance value. Thus, the outputs from the APFs may have substantially a zero phase difference between the voltage and current waveforms for real resistive tissue loads.

The resonance angular frequency $\omega_r$ is an angular frequency where the phase lag is 90° and is calculated according to the following equation:

$$\omega_r = \frac{1}{RC}.$$

The resonance frequency $f_r$ of the APF 550 is given by the following equation:

$$f_r = \frac{\omega_r}{2\pi}.$$

The group delay $t_{gd}$ is given by the following equation:

$$t_{gd} = \frac{2RC}{(\omega_c RC)^2 + 1}.$$

FIG. 5B shows a circuit of an APF 580 according to another embodiment that may be employed in the power calculation circuits of FIGS. 4A-4C. The APF 580 has leading phase, which is achieved by swapping the positions of the resistor 565 and the capacitor 560 in the APF 500 of FIG. 5A. Specifically, the APF 580 has the capacitor 560 connected between the non-inverting node 530 and ground, and has the resistor 565 connected between the input node 510 and the non-inverting node 530. The transfer function of the APF 580 is determined as follows:

$$H(s) = \frac{2\frac{1}{sC}}{R + \frac{1}{sC}} - 1 = \frac{2}{sRC + 1} - 1 = \frac{-sRC + 1}{sRC + 1} = -\frac{sRC - 1}{sRC + 1}.$$

As with the APF 500 of FIG. 5B, the gain of the APF 580 is one or may be adjusted through different ratios of R'.

In both APFs 500 and 580, the resistor 565 may be a variable resistor so that the resistance value R of the resistor 565 can be varied based on the frequency of the voltage or current waveform and/or the properties of the electrosurgical cable. In this way, the power dosage monitor can continuously adjust the variable resistor to achieve finer resolution calibration for the phase shift caused by the electrosurgical cable.

Alternatively, the resistance value R of the resistor 565 and the capacitance value C of the capacitor 560 of the APFs 500 and 580 may be fixed at manufacturing time for compensating for the nominal voltage-current phase shift:

$$\delta\phi_{VT} = (\Delta\phi_V \pm \Delta\phi_I),$$

where $\Delta\phi_V$ is the phase shift of the voltage waveform and $\Delta\phi_I$ is the phase shift of the current waveform.

First order APFs may be sufficient for compensation of most systems at the carrier frequency or even at most of the relevant harmonics of the carrier frequency. However, finer adjustments may be needed at these harmonics. For these cases, second order or higher order APFs may be employed in the power calculation circuits of FIGS. 4A-4C. FIGS. 6-9 show circuit diagrams of second order APFs according to embodiments of present disclosure.

Figure 5C:
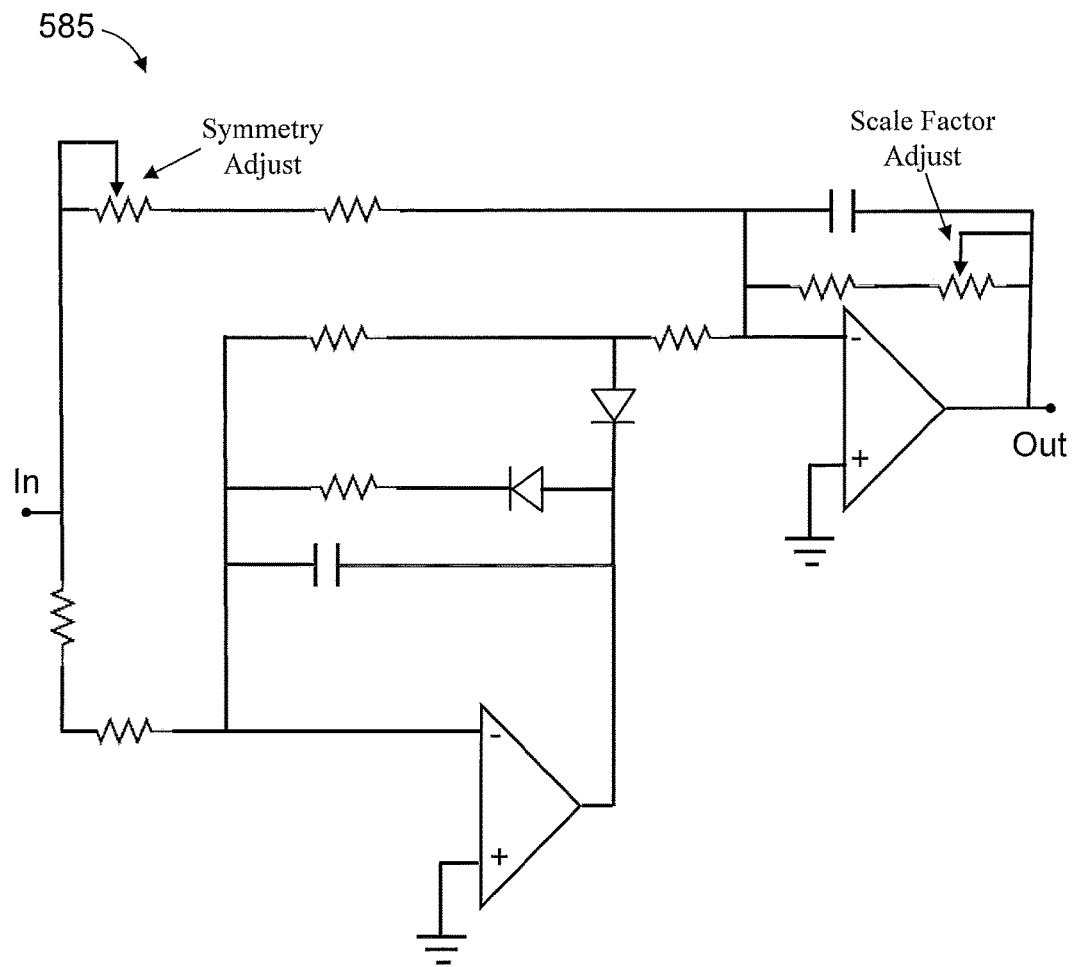
FIG. 5C is a circuit diagram of a MAD circuit 585 that may be employed in the power calculation circuit of FIG. 4B.

FIG. 5C is circuit diagram of a mean absolute deviation (MAD) circuit 585 that may be employed in the power calculation circuit of FIG. 4B. The MAD circuit 585 measures the magnitude of the AC signal that is input to the MAD circuit 585. The gain or scale factor of the MAD circuit 585 is calibrated to the ratio of RMS to MAD.

Figure 6:
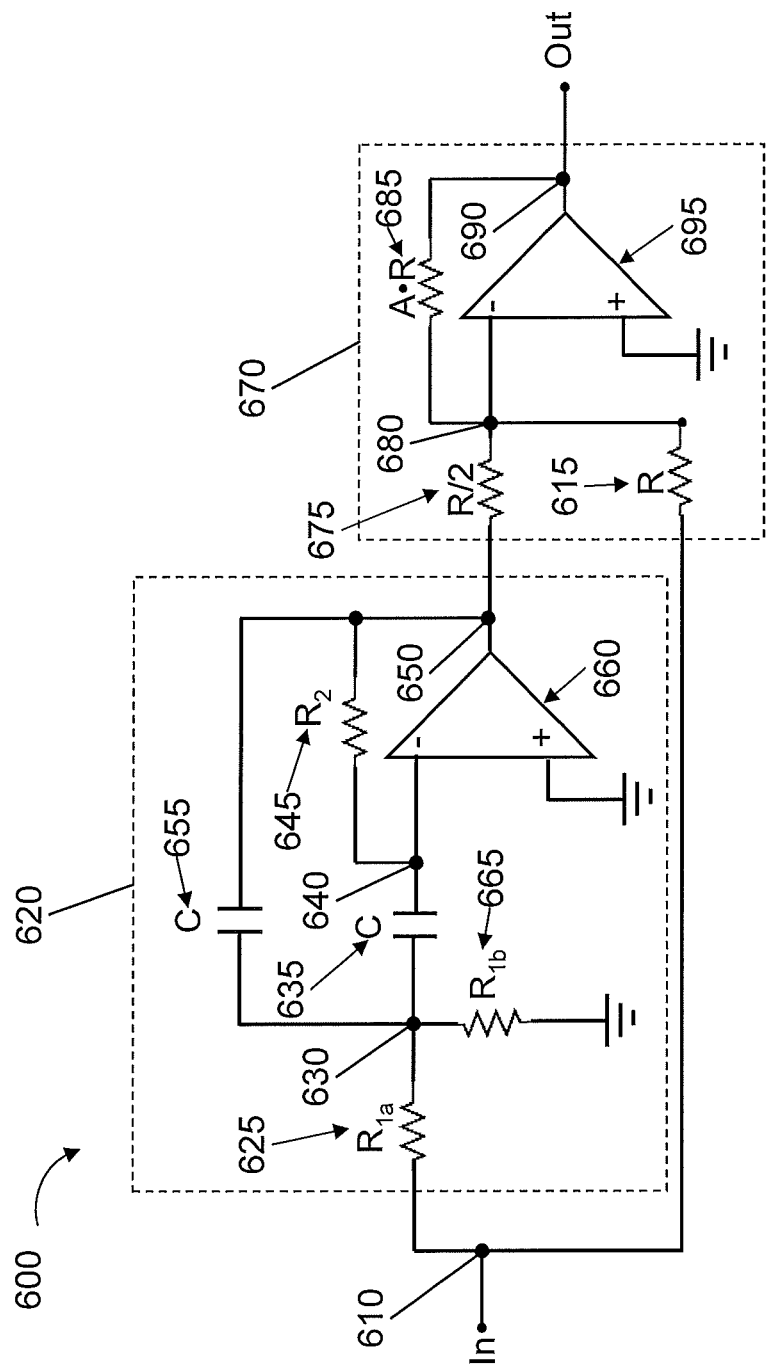
FIGS. 6-9 are circuit diagrams of second-order all-pass filters that may be employed in the power calculation circuits of FIGS. 4A-4C.

FIG. 6 shows a second order APF 600 that includes a multiple feedback bandpass (MFBP) filter 620 and an adder 670 having a gain A. The MFBP filter 620 includes an op-amp 660, resistors 625, 645, 665, and capacitors 635, 655 that are coupled together at various nodes including an input node 630, an inverting input node 640, and an output node 650. The non-inverting input of the op-amp 660 is grounded.

As shown in FIG. 6, the resistor 645 is connected between the output node 650 and the inverting input node 640 and the capacitor 635 is connected between the input node 630 and the inverting input node 640. The capacitor 655 is connected between the output node 650 and the input node 630. The resistor 645 and the capacitor 655 are connected to the op-amp in a negative feedback configuration, which gives a high quality factor to the MFBP filter 620. The resistor 665 is connected between the input node 630 and ground and the resistor 625 is connected between the input node of the APF 600 and the input node 630 of the MFBP filter 620.

The passband of the MFBP filter 620 is defined by two cutoff or corner frequencies at which the output of a circuit is −3 dB of the nominal passband value. The bandwidth of the MFBP filter 620 is then defined by the difference between the lower cutoff frequency $f_L$ and the higher cutoff frequency $f_H$, as follows:

$$BW = f_H - f_L.$$

The quality factor Q is a measure that characterizes a frequency response of a filter. The quality factor is the ratio of the resonant frequency $f_r$ to the bandwidth (BW) where the resonance frequency $f_r$ is the center frequency. A higher quality factor indicates that the frequency response has a narrower bandwidth and a higher gain, while a lower quality factor indicates that the frequency response has a wider bandwidth and a smaller gain.

The resistance values of the three resistors 625, 646, and 665 of the MFBP filter 620 are determined based on the quality factor Q of the MFBP filter 620. For example, when the quality factor Q of the MFBP filter 620 is greater than 0.707 and less than 20, the resistance values of the three resistors 625, 645, and 665 are determined according to the following equations:

$$R_2 = \frac{2Q}{\omega_r C} = \frac{Q}{\pi f_r C},$$

$$R_{1a} = \frac{R_2}{2}, \text{ and}$$

$$R_{1b} = \frac{R_{1a}}{2Q^2 - 1},$$

where $R_{1a}$ is the resistance value of the resistor 625, $R_{1b}$ is the resistance value of the resistor 665, $R_2$ is the resistance value of the resistor 645, and C is the capacitance value of the capacitor 635 or 655. The capacitance value C of the capacitor 635 or 655 can be chosen arbitrarily.

The maximum group delay of the MFBP filter 620 occurs at the resonant frequency $f_r$, which may be the carrier frequency or some other frequency of interest to be equalized. When the quality factor Q is greater than two, the resistance values of the three resistors 625, 646, and 665 are determined based on the group delay of the MFBP filter 620 as follows:

$$R_2 = \frac{t_{gd,max}}{2C},$$

$$R_{1b} = \frac{R_2}{(\pi f_r t_{gd,max})^2 - 1}, \text{ and}$$

$$R_{1a} = \frac{R_2}{2},$$

where $t_{gd,max}$ is the maximum group delay of the MFBP filter 620. The resistance value $R_{1b}$ may be varied to vary the group delay of the MFBP filter 620. The gain of the MFBP filter 620 should be maintained at unity to avoid ripple in the frequency response near the resonant frequency $f_r$.

The adder 670 of the APF 600 which provides an overall gain A includes three resistors 615, 675, 685, and an op-amp 695. The adder 670 has three nodes: and inverting input node 680, and output node 690, and a non-inverting input node which is grounded. The resistor 615 is connected between the input node 610 of the APF 600 and the inverting input node 680, the resistor 675 is connected between the output node 650 of the MFBP filter 620 and the inverting input node 680, and the resistor 685 is connected between the inverting input node 680 and the output node 690. The gain of the adder 670 is A and thus the gain of the second order APF 600 is A because the gain of the MFBP filter 620 is unity gain. Resistance values of the three resistors 615, 675, and 685 are R, R/2, and A*R, respectively. In this configuration, the gain of the adder is A which may be used to compensate for gain inaccuracies in the bandwidth of interest. The resistance value R of the resistor 615 may be chosen arbitrarily. With this configuration of the second order APF 600, the quality factor can be maintained below 20 and the maximum group delay is:

$$t_{gd,max} = \frac{40}{\pi f_r}.$$

Figure 7:
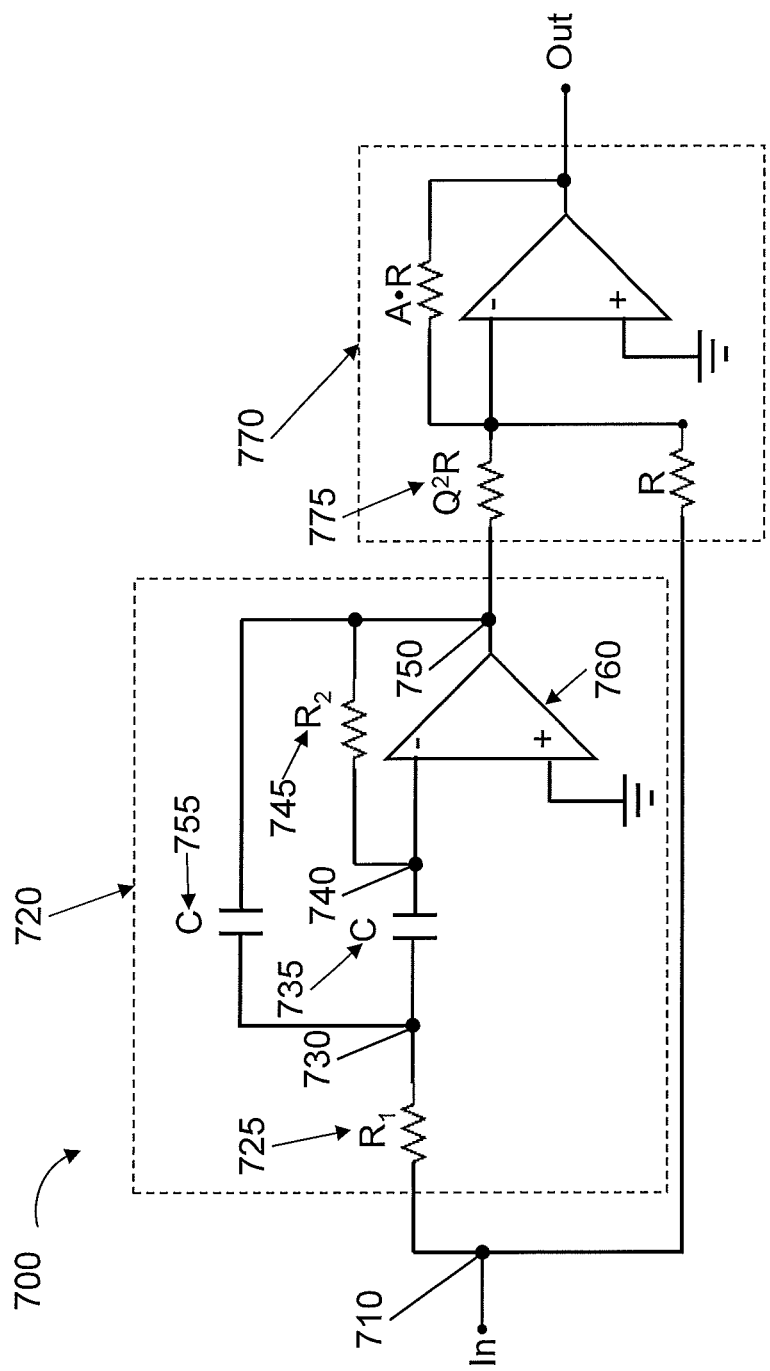

FIG. 7 shows a circuit diagram of a second order APF 700 according to another embodiment that may be employed in the power calculation circuits of FIGS. 4A-4C. The second order APF 700 includes a MFBP filter 720 and an adder 770 having a gain A. The configuration of the MFBP filter 720 is the same as the configuration of the MFBP filter 620 except that the MFBP filter 720 does not include the resistor 665 of the MFBP 620. In other words, the MFBP 720 does not have a resistor connected between the input node 730 of the MFBP 720 and ground. The resistance value $R_1$ of the resistor 725 is determined based on the resistance value $R_2$ of the resistor 745 as follows:

$$R_1 = \frac{R_2}{4Q^2},$$

where Q is the quality factor of the second order APF 700. The resistance value $R_1$ and the capacitance value C of the two capacitors 735 and 755 can be chosen arbitrarily.

The configuration of the adder 770 is the same as that of the adder of the second order APF 600 except that the resistance value of the resistor 775, which corresponds to the resistor 675 of FIG. 6, is $Q^2 R$. With this configuration of the MFBP 720 and the adder 770, the second order APF 700 can maintain a quality factor Q of less than 0.707.

Figure 8:
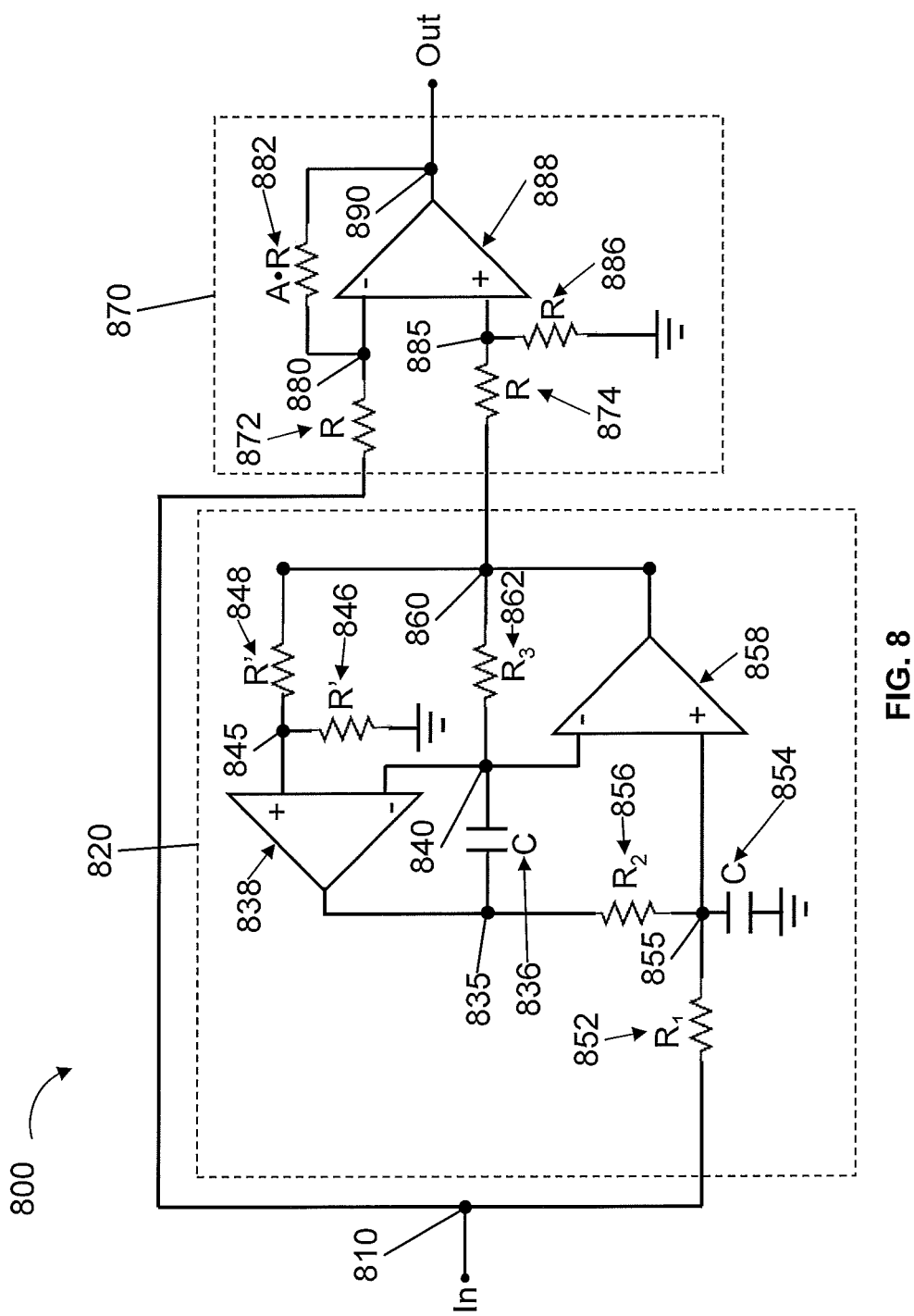

FIG. 8 shows another embodiment of a second order APF 800 that may be employed in the power calculation circuits of FIGS. 4A-4C. The second order APF 800 includes a dual amplifier bandpass (DABP) filter 820 and a differential amplifier 870. The DABP filter 820 is useful in designs requiring high quality factors and high frequencies. The DABP filter 820 includes two op-amps 838, 858, resistors 846, 848, 852, 856, 862, and capacitors 836, 854, which are connected to each other at various nodes include a node 835, an inverting input node 840, a first non-inverting input node 845, a second non-inverting input node 855, and a first output node 860.

As shown in FIG. 8, the resistor 852 is connected between the input node 810 and the non-inverting input node 855 of the DABP filter 820; the capacitor 854 is connected between the non-inverting input node 855 and ground; the resistor 856 is connected between the non-inverting input node 855 and the node 835; the capacitor 836 is connected between the node 835 and the inverting input node 840; the resistor 862 is a feed back resistor connected between the inverting input node 840 and the output node 860; the resistor 848 is connected between the output node 860 and the non-inverting input node 845; and the resistor 846 is connected between the non-inverting input node 845 and ground.

The differential amplifier 870 includes an op-amp 888 and resistors 872, 874, 882, 886 which are connected to one or more of three nodes including an inverting input node 880, a non-inverting input node 885, and a second output node 890. The resistor 872 is connected between the input node 810 and the inverting input node 880; the resistor 882 is a feedback resistor connected between the inverting input node 880 and the second output node 890; the resistor 874 is connected between the first output node 860 of the DABP filter 860 and the non-inverting input node 885; and the resistor 886 is connected between the non-inverting input node 885 and ground. As shown in FIG. 8, the resistance values of the resistors 872, 874, 886 are equal to R and the resistance value of the resistor 882 is A*R where A is the gain. The gain A may be used to compensate for gain inaccuracies in the bandwidth of interest.

The differential amplifier 870 amplifies the difference between voltages at the inverting input node 880 and non-inverting input node 890. As described above, the gain of the DABP filter 820 is 2. Thus, when $V_{in}$ is applied to the input node 810, the output voltage of the DABP filter 820 is $2*V_{in}$. Thus, the voltage $V_+$ at the non-inverting input node 885 and the output voltage $V_{out+}$ at the output node 890 caused by the voltage $V_+$ are calculated as follows:

$$V_+ = 2V_{in} \cdot \frac{R}{R+R} = V_{in}, \text{ and}$$

$$V_{out+} = V_+ \cdot \frac{R + A \cdot R}{R} = V_{in}(1 + A).$$

The output voltage $V_{out-}$ at the output node 890 caused by the voltage V at the inverting node 880 is calculated as follows:

$$V_{out-} = V_{in} \cdot \left(-\frac{A \cdot R}{R}\right) = -A \cdot V_{in}.$$

Then, the output voltage $V_{out}$ of the differential amplifier 870 is the sum of voltages $V_{out+}$ and $V_{out-}$ as follows:

$$V_{out} = V_{out+} + V_{out-} = V_{in} \cdot (1+A) + V_{in} \cdot (-A) = V_{in}.$$

Thus, the second order AFP 800 has the gain of one.

The resistance value R' of the resistors 846, 848, the capacitance value C of the capacitors 836, 854, and the resistance value R can be chosen arbitrarily. The resistance value of the resistors 852, 856, and 862, are calculated according to the following equations:

$$R_1 = \frac{Q}{2\pi f_r C}, \text{ and}$$

$$R_2 = R_3 = \frac{R_1}{Q},$$

where $R_3$ is the resistance value of the resistor 862. With this configuration, the DABP 820 can maintain a quality factor Q of up to 150. The group delay may be varied by varying the resistance $R_3$ of resistor 862 using a variable resistor. The quality factor Q and the group delay of the DABP 820 may be simultaneously varied by varying the resistance value $R_1$ of resistor 852 using a variable resistor.

Figure 9:
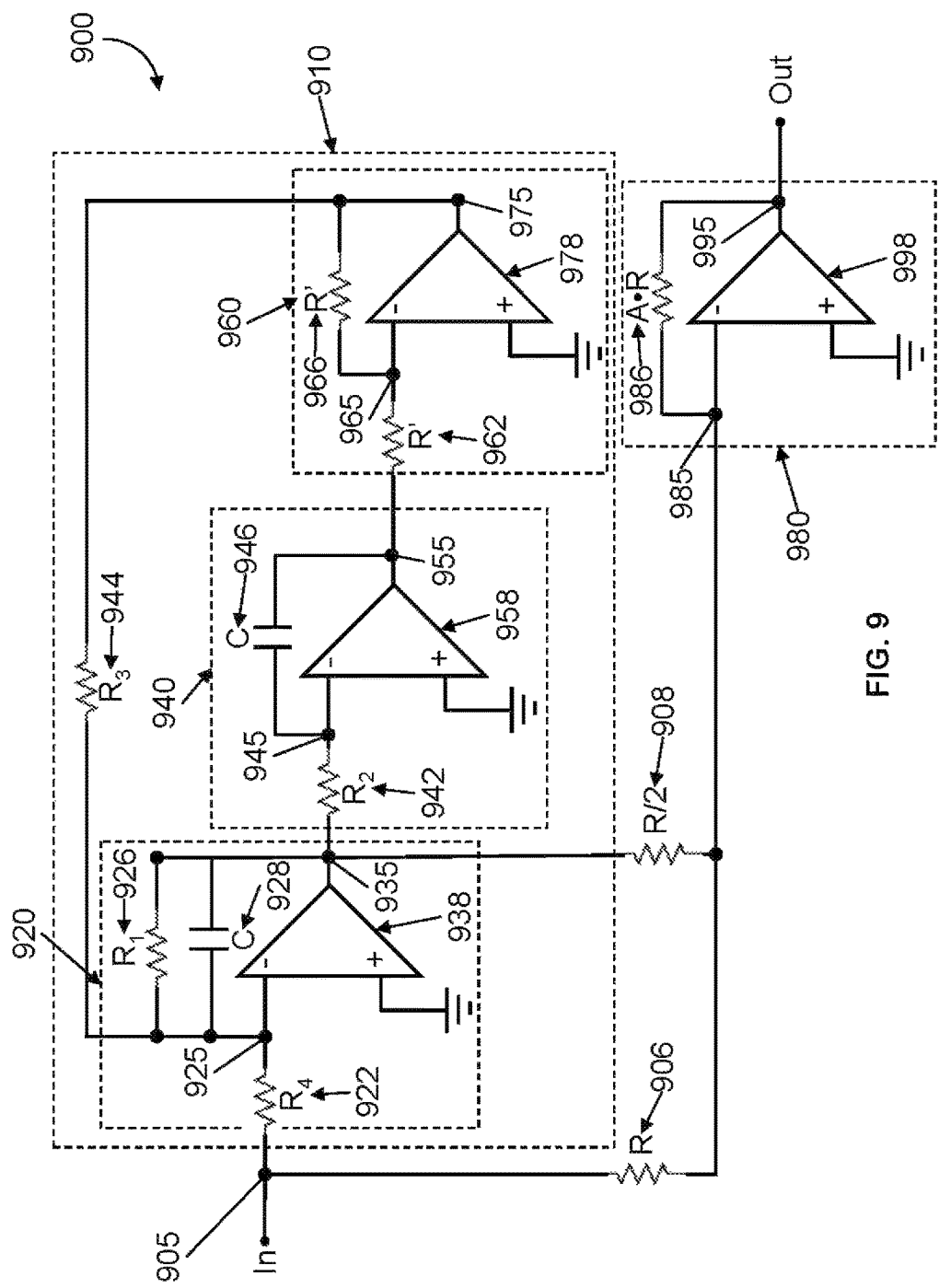

FIG. 9 shows another embodiment of a second order APF 900 that may be employed in the power calculation circuits of FIGS. 4A-4C. The second order APF 900 uses an adder 980 having a gain A and a biquad equalizer 910 that includes integrators 920, 940 and a differential amplifier 960. The integrator 920 includes resistors 922, 926, a capacitor 928, and an op-amp 938, which are connected to one or more nodes including an inverting input node 925, an output node 935, and a non-inverting node which is grounded. The resistor 922 is connected between the input node 925 and the inverting input node 925. The resistor 926 and the capacitor 928 are connected between the inverting input node 925 and the output node 935.

The integrator 940 includes a resistor 942, a capacitor 946, and an op-amp 958, which are connected to one or more nodes including an inverting input node 945, an output node 955, and a non-inverting input node which is grounded. The resistor 942 is connected between the output node of the integrator 920 and the inverting input node 945. The capacitor 946 is connected between the inverting input node 945 and the output node 955.

The differential amplifier 960 includes two resistors 962, 966 and an op-amp 978, which are connected to one or more nodes including an inverting input node 965, an output node 975, and a non-inverting input node which is grounded. The resistor 962 is connected between the output node 955 of the integrator 940 and the resistor 966 is connected between the inverting input node 965 and the output node 975. A resistor 944 is a feedback resistor connected between the inverting input node 925 of the integrator 920 and the output node 975 of the differential amplifier 960.

The biquad equalizer 910 may have three outputs from the two integrators 920 and 940 and the differential amplifier 960. The output node 935 of the integrator 920 provides a bandpass output voltage, and the output nodes 955, 975 of the integrator 940 and the differential amplifier 960 provide a low-pass output voltage. Since the second order APF 900 uses the bandpass output, the output of the integrator 920 is used. However, the other outputs may be used for other purposes.

The adder 980 having a gain A includes a resistor 986 and an op-amp 998 which are connected to one or more nodes including an inverting input node 965, an output node 975, and a non-inverting input node which is grounded. The resistor 986 is connected between the inverting input node 985 and the output node 995. A resistor 906 is connected between the inverting input node 965 and the inverting input node 985 of the adder 980. Another resistor 908 is connected between the output node 935 of the integrator 920 and the inverting input node 985 of the adder 980.

Resistance values of the resistors 906 and 962, the capacitance value of the capacitor 928, and the gain A may be chosen arbitrarily. Here, the resistance value $R_3$ of the resistor 944 may be variable for changing the group delay of the biquad equalizer 910. Since changes to the resistance value R3 also changes the quality factor Q, the resistance value R3 may have to be simultaneously adjusted to maintain the quality factor Q. Resistance values of the other resistors are determined as follows:

$$R_1 = R_4 = \frac{Q}{2\pi f_r C}, \text{ and}$$

$$R_2 = R_3 = \frac{R_1}{Q},$$

where R1, R2, R3, and R4 are resistance values of the resistors 926, 942, 944, and 922, respectively. With this configuration, the biquad equalizer 910 may maintain the quality factor Q up to 200.

Figure 10:
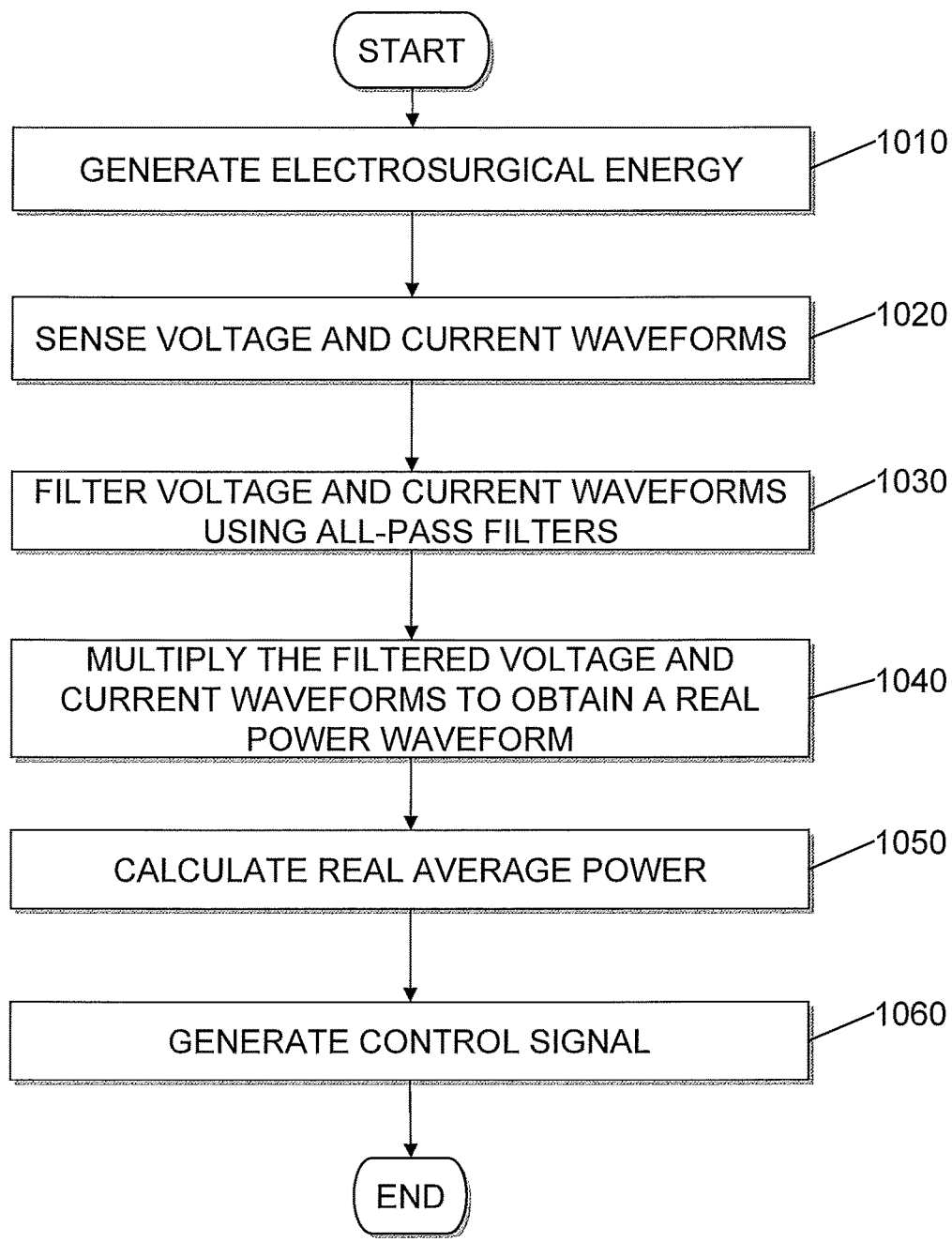
FIG. 10 is a flow diagram of a method of monitoring average real power output from an electrosurgical generator in accordance with embodiments of the present disclosure.

FIG. 10 is a flow chart illustrating a method for monitoring power dosage according to embodiments of the present disclosure. This method may be implemented by using both digital and analog circuits. The method first compensates for the phase shift caused by a circuit network including an electrosurgical generator and a cable connected to deliver electrosurgical energy to treat tissue using analog circuitry, and then calculates the power delivered to and consumed by the tissue using digital circuitry.

The electrosurgical generator generates electrosurgical energy in step 1010 that may be in a form of alternating voltage and current waveforms. In step 1020, sensors sense the voltage and current waveforms. In step 1030, analog all-pass filters (APFs) filter the voltage and current waveforms. Since the generated voltage and current waveforms may have a phase shift and gain inaccuracy caused by the circuit network and the APFs also includes a phase delay and gain, the APFs may be designed in a way so that the phase delay of the APFs can compensate for the phase shift and the gains compensated. In this way, the output of the APFs has substantially a zero phase difference between the voltage and current waveforms and no inaccuracy in the gains.

In step 1040, the gain and phase-compensated voltage and current waveforms are multiplied to provide an analog power waveform. Due to the substantially zero phase difference, the analog power waveform is real and not complex. This analog power waveform is provided to the digital circuitry that computes real average power in step 1050. The controller of the electrosurgical generator then compares the computed real average power with a predetermined power profile that is specific for an electrosurgical operation and generates a control signal in step 1060. Steps 1010-1060 are continuously performed until a user of the electrosurgical generator terminates the operation or disconnects the cable from the electrosurgical generator.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. An electrosurgical generator comprising:
   an output stage configured to generate electrosurgical energy;
   a plurality of sensors configured to sense a voltage waveform and a current waveform of the generated electrosurgical energy;
   a plurality of analog all-pass filters configured to filter the sensed voltage and current waveforms;
   an analog multiplier configured to multiply the filtered voltage and current waveforms to obtain a real power waveform;
   an average power calculation circuit configured to calculate a real average power based on the real power waveform; and
   a controller configured to generate a control signal to control the output stage based on the real average power,
   wherein the plurality of analog all-pass filters include a resistor and a capacitor having values that cause the plurality of analog all-pass filters to compensate for a phase difference between the voltage waveform and the current waveform.

2. The electrosurgical generator according to claim 1, wherein the average power calculation circuit includes:
   an analog integrator configured to integrate the real power waveform;
   an analog-to-digital converter (ADC) configured to convert the integrated real power waveform into digital power waveform data; and a digital averaging filter configured to calculate the real average power based on the digital power waveform data.

3. The electrosurgical generator according to claim 2, wherein the digital averaging filter is a moving average filter.

4. The electrosurgical generator according to claim 3, wherein the moving average filter is a finite impulse response filter or an infinite impulse response filter.

5. The electrosurgical generator according to claim 1, wherein the average power calculation circuit includes:
an analog low pass filter configured to filter the real power waveform;
an analog-to-digital converter (ADC) configured to digitally sample the filtered power waveform into digital power waveform data; and
a digital integrator configured to integrate the digital power waveform data to calculate the real average power.

6. The electrosurgical generator according to claim 1, wherein each of the plurality of analog all-pass filters has a lagging phase or a leading phase.

7. The electrosurgical generator according to claim 1, wherein the resistor is a variable resistor to continuously adjust the phase difference between the voltage waveform and the current waveform.

8. The electrosurgical generator according to claim 1, wherein the plurality of analog all-pass filters are first-order all-pass filters or second-order all-pass filters.

9. The electrosurgical generator according to claim 8, wherein the second-order all-pass filters include at least one bandpass filter.

10. The electrosurgical generator according to claim 9, wherein the bandpass filter is a multiple feedback bandpass filter, dual amplifier bandpass filter, or biquad filter.

11. A method for controlling an electrosurgical generator, the method comprising:
generating, by an output stage, electrosurgical energy;
sensing a voltage waveform and a current waveform of the generated electrosurgical energy;
filtering the sensed voltage and current waveforms by a plurality of analog all-pass filters;
multiplying the filtered voltage and current waveforms to obtain a real power waveform;
calculating a real average power based on the real power waveform; and
generating a control signal to control the output stage based on the real average power,
wherein the plurality of analog all-pass filters include a resistor and a capacitor having values that cause the plurality of analog all-pass filters to compensate for a phase difference between the voltage waveform and the current waveform.

12. The method according to claim 11, wherein multiplying the filtered voltage includes:
integrating the real power waveform by an analog integrator;
converting the integrated real power waveform into digital power waveform data; and
calculating the real average power based on the digital power waveform data.

13. The method according to claim 11, wherein multiplying the filtered voltage includes:
filtering the real power waveform by using an analog low pass filter;
converting the filtered real power waveform into digital power waveform data; and
integrating the digital power waveform data to calculate the real average power.

14. The method according to claim 11, wherein each of the plurality of analog all pass-filter has a lagging phase or a leading phase.

15. The method according to claim 11, wherein the resistor is a variable resistor.

16. The method according to claim 15, further comprising:
adjusting a resistance value of the variable resistor to continuously compensate for the phase difference between the voltage waveform and the current waveform.

17. A non-transitory computer-readable medium storing instructions that, when executed by a processor, implement a method for controlling an electrosurgical generator, the method comprising:
generating, by an output stage, electrosurgical energy;
sensing a voltage waveform and a current waveform of the generated electrosurgical energy;
filtering the sensed voltage and current waveforms by a plurality of analog all-pass filters;
multiplying the filtered voltage and current waveforms to obtain a real power waveform;
calculating a real average power based on the real power waveform; and
generating a control signal to control the output stage based on the real average power,
wherein the plurality of analog all-pass filters include a resistor and a capacitor having values that cause the plurality of analog all-pass filters to compensate for a phase difference between the voltage waveform and the current waveform.

* * * * *